United States Patent [19]

Miyao et al.

[11] Patent Number: 4,973,553
[45] Date of Patent: Nov. 27, 1990

[54] SALT OR ORGANOGERMANIUM COMPOUND AND MEDICINE CONTAINING THE SAME

[75] Inventors: Kohei Miyao; Hiroshi Satoh, both of Tokyo; Norihiro Kakimoto, Machida, all of Japan

[73] Assignee: Asai Germanium Research Institute, Tokyo, Japan

[21] Appl. No.: 92,900

[22] Filed: Sep. 4, 1987

[51] Int. Cl.$^5$ .................... C12N 9/36; C07F 7/30; A61K 37/54; A61K 31/195
[52] U.S. Cl. .................... 435/206; 424/94.61; 424/650; 556/81; 556/87; 556/88; 514/561
[58] Field of Search .................... 424/650, 94.61; 435/206; 556/87–88, 81

[56] References Cited

U.S. PATENT DOCUMENTS

| | | | |
|---|---|---|---|
| 1,909,070 | 5/1933 | Parr | 424/650 |
| 4,361,579 | 11/1982 | Munakata et al. | 514/825 |
| 4,772,628 | 9/1988 | Kakimoto et al. | 556/87 |

FOREIGN PATENT DOCUMENTS

| | | | |
|---|---|---|---|
| 91114 | 10/1983 | European Pat. Off. | 514/492 |
| 102895 | 6/1982 | Japan | 424/650 |
| 2007975 | 5/1979 | United Kingdom | |
| 1550227 | 8/1979 | United Kingdom | |
| 2143128 | 2/1985 | United Kingdom | 514/492 |

OTHER PUBLICATIONS

Matsuoka, Chem. Abstracts, vol. 79:106541y (1973).

*Primary Examiner*—Jacqueline Stone
*Attorney, Agent, or Firm*—Burns, Doane, Swecker & Mathis

[57] ABSTRACT

The present invention provides salts of organogermanium compounds expressed by the following Formual (a):

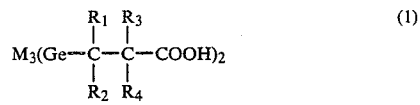

(wherein M denotes an oxygen or sulfur atom; and $R_1$, $R_2$, $R_3$, and $R_4$ may be the same or different from each other and each denotes a hydrogen atom, a lower alkyl group, or an aryl group) with compounds having basic groups, and medicines containing the salts such as biological response modifiers and antitumor agents.

28 Claims, 3 Drawing Sheets

SALT OR ORGANOGERMANIUM COMPOUND AND MEDICINE CONTAINING THE SAME

DETAILED DESCRIPTION OF THE INVENTION

1. Field of the Invention

The present invention relates to novel salts of organogermanium compounds and medicines containing those salts.

2. Prior Art and Problems

As shown in the literature such as "Pharmaceutical Activity of Organogermanium Compound Ge-132 (Introduction)" by Hiroshi Satoh and Kohei Miyao and "Inhibition of Tumor Growth and Metastasis in Association with Modification of Immune Response by Novel Organic Germanium Compounds", J. of Biological Response Modifiers, 4, 159–168 (1985) by Nobuo Tanaka, et al., organic germanium compounds expressed by Formula (1) exhibit excellent characteristics as biological response modifiers. For example, they are active in inducing interferon, can activate macrophage or NK cells, and have antitumor activities based thereon. In addition, since these compounds exhibit desirable pharmaceutical activities such as an ability to control enkephalin-degrading enzymes and improve Ca metabolism, and also have a low level of toxicity, it is thought that they can be used as useful pharmaceuticals.

However, since the compounds expressed by Formula (1), such as carboxyethylgermanium sesquioxide (i.e. $O_3(GeCH_2CH_2COOH)_2$ in which M in Formula (1) is an oxygen atom and $R_1$ to $R_4$ are each a hydrogen atom, and which is referred to as Ge(O,H) hereinafter) generally have a low solubility in water and thus do not easily dissolve in usual organic solvents, they cannot be directly prepared as liquid medicines such as solutions for injection. In addition, when orally administered, they have disadvantages with respect to their low levels of bioavailability and their short half-life in blood due to their extremely low absorption efficiency.

However, since the above-described compounds have carboxyl groups, it should be possible to change them into water-soluble compounds by neutralizing them. For example, the neutralization of the above-described Ge(O,H) with sodium bicarbonate ($NaHCO_3$) or sodium hydroxide (NaOH) enables the preparation of an aqueous solution containing 10% by weight of Ge(O,H).

Since an inorganic salt of the above-described Ge-(O,H), such as sodium (Na), potassium (K), or calcium (Ca) salt, has very poor crystallinity and is hygroscopic, it cannot be obtained as crystals. In addition, since the Ge(O,H) is a weak acid, the aqueous solution obtained by its complete neutralization with an inorganic base is alkaline.

MEANS FOR SOLVING THE PROBLEMS

The present invention has been accomplished as a result of energetic research conducted by the inventors of the present invention with a view to solving the above-described drawbacks of the known compounds.

The inventors have made an effort to ensure that the above-described compounds are safe, in view of the fact that they will be used as pharmaceuticals.

The present invention relates to salts of organogermanium compounds expressed by the following Formula (1):

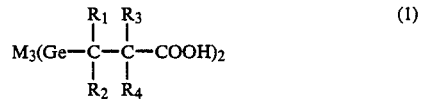

(wherein M denotes an oxygen or sulfur atom; and $R_1$, $R_2$, $R_3$, and $R_4$ may be the same or different from each other and each denotes a hydrogen atom, a lower alkyl group, or an aryl group) with compounds having basic groups.

A description will illustrate of the above-described organogermanium compounds.

These compounds have basic skeletons in which propionic acid derivatives having substituents $R_1$, $R_2$, Rhd 3, and $R_4$ are bonded to germanium atoms, the germanium atoms in the basic skeletons being bonded to oxygen atoms (when M=0) or sulfur atoms (when M=S) in the ratio of 2 : 3.

The substituents $R_1$, $R_2$, $R_3$, and $R_4$ may be the same or different and each denotes a hydrogen atom, a lower alkyl group such as a methyl, ethyl, propyl, or butyl group, or an aryl group such as a phenyl group.

The substituents $R_1$ and $R_2$ are bonded to the carbon atom at the $\alpha$-position with respect to the germanium atom and the substituents $R_3$ and $R_4$ are bonded to the carbon atom at the $\beta$-position with respect to the germanium atom.

Lysozymes can be first exemplified as compounds having basic groups used for forming salts with the above-described organogermanium compounds.

Lysozymes, which are pure basic zymoproteins having a high level of stability, are generally present in various tissues of many kinds of plants and animals, including humans, function as natural protective substances, and are used as pharmaceuticals. A lysozyme has the structure of a simple polypeptide comprising 20 different kinds of 129 amino acid subunits which are brige-bonded by 4 disulfide bridges, and has a molecular weight of about 14,400±100 and shows an isoelectric point at a pH of 10.5 to 11.0.

In addition, in the present invention, the COOH groups of each of the organogermanium compounds are bonded to free amino acids of the lysozyme molecules, or all or part of the basic groups thereof, such as guanidine groups or imidazole groups.

The salts of the present invention can be easily produced by reactions between the compounds expressed by Formula (1) and lysozymes, in accordance with conventional reactions between acids and bases. The reaction products obtained are crystalline and thus can be separated out or recrystallized from, for example, a system of water and alcohol.

For example, since the neutral salt produced from the Ge(O,H) and a lysozyme has good crystallinity and gradually dissolves in solvents, it has an effect of sustained release and can be maintained as a long-lasting medicine at a certain concentration in the blood by a device, such as a gastric retention type of medicine, so that this salt can be prepared as medicines which have high levels of bioavailability.

Basic amino acids can also be used as compounds having basic groups.

Examples of basic amino acids used in the present invention include L-lysine, L-arginine, and L-histidine. In this case, in the present invention, the COOH groups of the organogermanium compounds are bonded to amino or imino groups of basic amino acids.

The above-described salts of the present invention can be easily produced with a good yield by the reactions between the compounds expressed by Formula (1) and basic amino acids, in accordance with conventional reactions between acids and bases. For example, equivalent amounts of a compound expressed by Formula (1) and a basic amino acid are mixed together and the mixture is dissolved in as little water as possible under heating. Crystals are separated out by filtering the thus-produced solution then cooling it, or by concentrating the reaction solution, or the salt is separated out by adding an organic solvent such as ethanol to the concentrated aqueous solution, and the salt is then filtered off and dried. The thus-obtained salt of the present invention is excellent in crystallinity, unlike the salts with inorganic bases described above. When prepared, this salt therefore has desirable physical properties as a principal ingredient of a solid medicine in a form such as tablets, granules, or capsules. In addition, this salt is extremely water-soluble, unlike the compounds expressed by Formula (1), and thus can be used as it is in the preparation of liquid medicines containing appropriate concentrations of the salt (for example, 2 to 20% by weight, preferably about 3 to 7% by weight, measured as organogermanium compounds). Unlike salts with inorganic bases, aqueous solutions of the salts of the present invention have a pH of about 7, which is within the range of biological pH values.

The pH of about 7 of aqueous solutions of the salts of the present invention means that these solutions exhibit strong buffer actions, and, when the salts are orally administered, free organogermanium compounds are separated out therefrom at a much lower rate when they come into contact with acids in the stomach. On the other hand, when salts with inorganic bases are orally administered, free organogermanium compounds have a tendency to be immediately separated out by the acids in the stomach from the aqueous solutions of the salts, which are thus made insoluble, resulting in a reduction in the efficiency with which they are absorbed in the body, and thus a reduction in their bioavailability. Therefore, since the salts of the present invention are present as molecules or very fine particles, without any separation of the organogermanium compounds, they exhibit excellent levels of absorptivity and thus an increased efficiency of absorption into the body, resulting in an increase in their bioavailability.

The present invention also relates to biological response modifiers comprising salts produced from the organogermanium compounds expressed by Formula (1) and compounds having basic groups.

Biological response modifiers (referred to as modifiers hereinafter) of the present invention have higher levels of bioavailability than those of conventional organogermanium compounds or salts thereof. For example, some of these modifiers are excellent for activating macrophage or NK cells, or inducing interferon.

The modifiers of the present invention are much more active in producing biological response modifications than the compounds expressed by Formula (1). Namely, in DHT (delayed type hypersensitive reaction) by a foot-padding method, Ge(O,H) and a lysozyme salt thereof exhibited increased effects which were 108% and 116% relative to a control, respectively, when administered in doses of 100 mg/kg.

The modifiers of the present invention, therefore, have excellent levels of availability compared with conventional organogermanium compounds alone.

The present invention also relates to antitumor agents comprising salts of the organogermanium compounds expressed by Formula (1) with compounds having basic groups.

As described above, the salts of the present invention have higher levels of bioavailability than those of conventional organogermanium compounds or salts thereof, and thus exhibit excellent antitumor actions.

When animal experiments on rats were performed, salts which were administered in doses of about half those of the organogermanium compounds alone exhibited similar antitumor effects. Therefore, the medicines of the present invention can be used in oral or parenteral administration, according to symptoms and can be prepared into forms which are conventionally used for oral or parenteral administration, such as liquids, powders, fine particles, granules, tablets, coated tablets, capsules, injections, ointments, or creams. Such forms can be prepared by mixing the salts produced from the organogermanium compounds expressed by Formula (1) and compounds having basic groups with additives conventionally used in preparations, such as excipients, fillers, binders, disintegrators, lubricants, perfumes, tinctures, or sterile water.

The medicines of the present invention can be administered to adults one to more times per day at a total dosage of the active component of 20 to 100 mg/kg, preferably 30 to 70 mg/kg per day, according to the symptoms.

The medicines of the present invention have virtually no toxicity. In particular, the lysozymes and amino acids which are the basic components are natural components and are used as pharmaceuticals such as oral medicines or injections. Since the safety and availability of these substances have thus been fully proven, these substances will present no problem when used as components of medicines.

DESCRIPTION OF EXAMPLES

Examples are described below.

EXAMPLE 1

Figure 1:
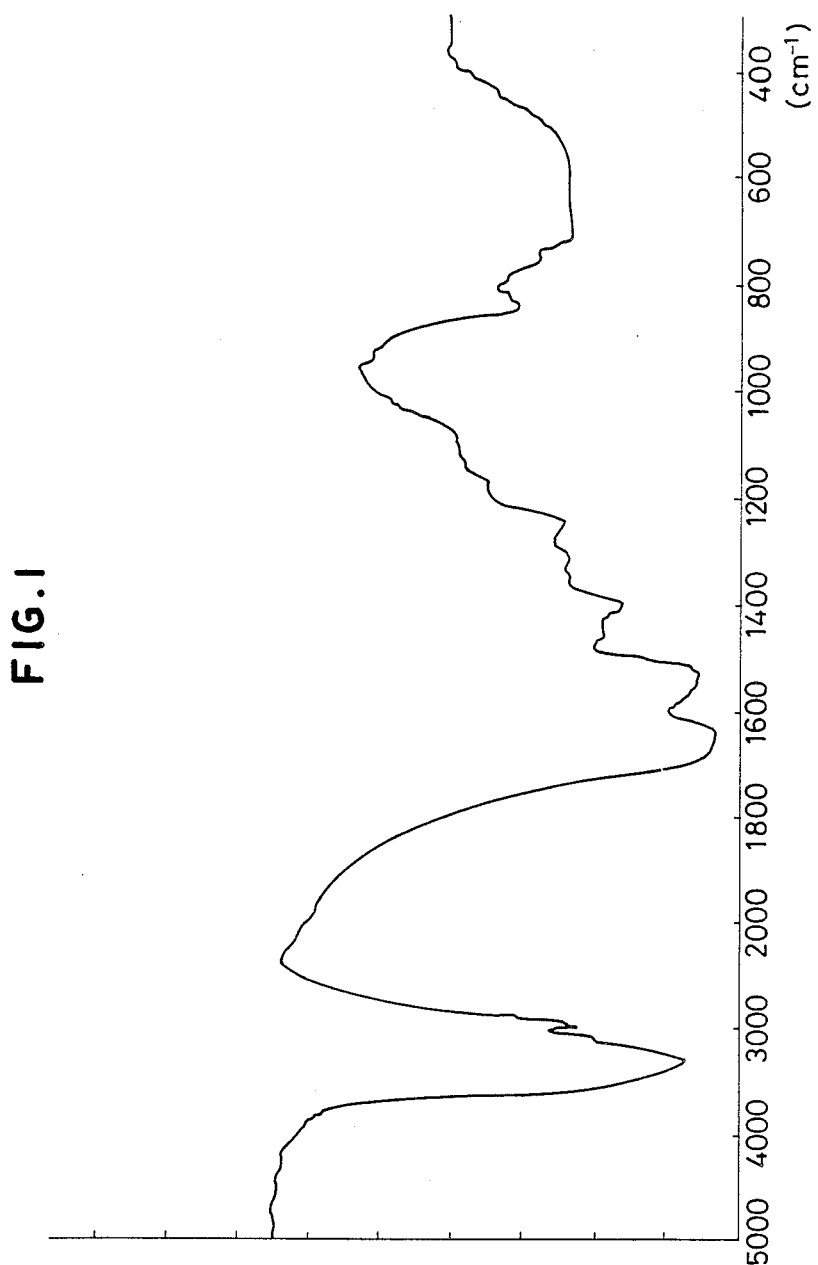
FIG. 1 is an IR spectrum of the compound obtained by Example 1.

14.7 g of lysozyme chloride was dissolved in a small amount of water and the resultant solution was passed through a column of liberation-type basic ion exchange resins. The column was then washed with water to obtain free lysozymes (pH 10). 1.35 g of carboxyethylgermanium sesquioxide was added to the thus-obtained aqueous solution under agitation and was dissolved therein. About ten times the volume of the obtained solution of ethanol was gradually added to the solution to separate out the reaction products. The products were filtered off then dried in a desiccator to obtain the intended substance as a colorless crystalline powder (yield, 92%; melting point, 300° C. or more (decomposition)). The IR spectrum of the substance is shown in FIG. 1.

EXAMPLE 2

Figure 2:
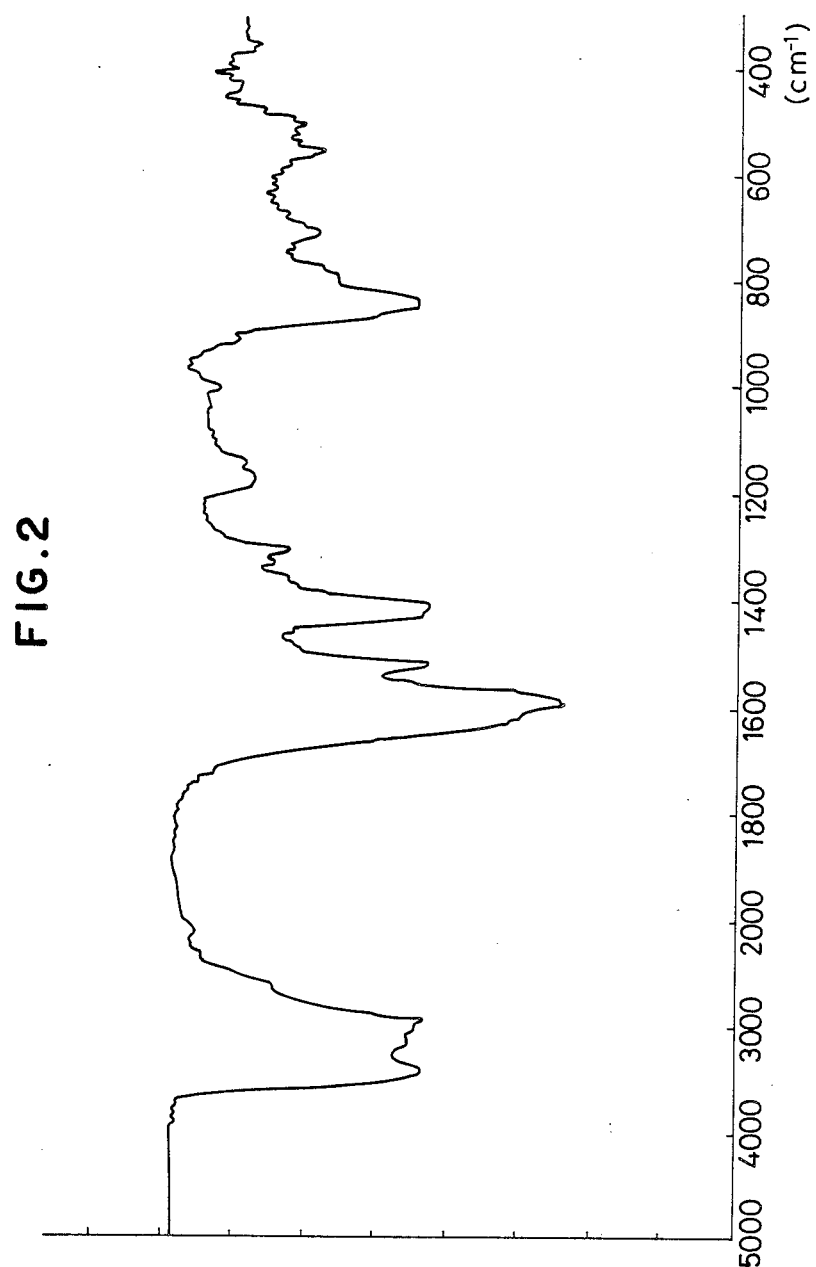
FIG. 2 is an IR spectrum of the compound obtained by Example 2.

19.6 g of L-lysine and 16.5 g of carboxyethylgermanium sesquioxide were dissolved in a small amount of hot water under agitation. Insoluble solids were filtered out and the filtrate was then gradually added to ten times its volume of ethanol under agitation to separate out the salt produced. This salt was allowed to stand in a refrigerator until it was completely separated out, then it was filtered. The thus-obtained crystals were dried in a vacuum desiccator to obtain the intended substance as a colorless fine crystalline powder (yield, 73%; melting point, 270° C. or more (decomposition)). The IR spectrum of the substance is shown in FIG. 2.

EXAMPLE 3

| Component | Amount (mg/tablet) |
| --- | --- |
| Carboxyethylgermanium sesquioxide lysozyme salt | 50 |
| Sodium carboxymethyl cellulose | 140 |
| Lactose | 40 |

Amounts of carboxyethylgermanium sesquioxide lysozyme salt and the additives corresponding to 5 tablets were each weighed then they were uniformly mixed together. The thus-obtained mixture was weighed to amounts corresponding to single tablets then was directly formed into tablets by a tablet machine at a pressure of 200 kg/cm$^2$ to obtain tablets. These tablets contained 50 mg of carboxyethylgermanium sesquioxide lysozyme salt as an active component per tablet.

EXAMPLE 4

8-week old ICR mice were used as test animals in groups of 6 mice. However, a control group comprised 12 mice. $10^8/0.05$ ml of sheep red blood corpuscles (SR8C) was injected under the plantar skin of each of the mice, and the same amount of SR8C was injected under the skin 4 days later. The next day, i.e., after 5 days, the increase in the thickness of the plantar of each mouse was measured.

The mice were divided into 3 groups comprising group A to which 100 mg/kg of the lysozyme salt of carboxyethylgermanium sesquioxide was orally administered once a day for 4 days after the start of the experiment, group B to which only carboxyethylgermanium sesquioxide was administered in a similar manner, and group C as a control group. The results of treatment are shown in Table 1.

TABLE 1

| Group | Increase in thickness of plantar | Increase ratio |
| --- | --- | --- |
| A | 2.9 ±1.4 mm | 116% |
| B | 2.7 ±1.2 mm | 108% |
| C | 2.5 ±1.8 mm | 100% |

EXAMPLE 5

A comparison was made between a lysine salt of carboxyethylgermanium sesquioxide (A) and carboxyethylgermanium sesquioxide (B) with respect to their antitumor effects on ascites hepatoma (AH66) of rats.

Female Donryu rats (each having a body weight of 120 to 150 g) were used, divided into three groups comprising a control group, administration group A, and administration group B, each containing six rats. A suspension ($10^7$/ml) of ascites hepatoma (AH66) cells of rats was prepared. 72 hours after an infusion graft of 1 ml of the suspension onto the tail vein of each rat, medicines (A) and (B) were administered to administration groups A and B, respectively. 100 mg/kg of each medicine was orally administered once a day for 10 days. Medicine (A) was used in the form of a 10 wt% aqueous solution, and Medicine (B) was used in the form of a 10 wt% suspension in an aqueous solution of 0.5 wt% of carboxymethyl cellulose.

Figure 3:
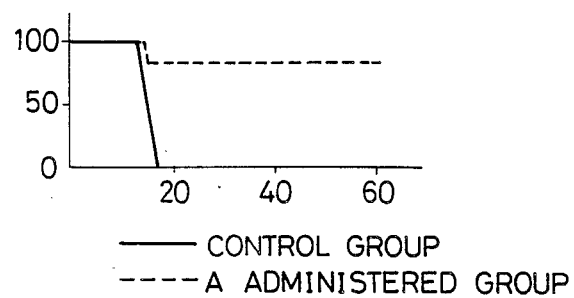
FIGS. 3 and 4 are survival graphs of rats obtained by Example 5.
Figure 4:
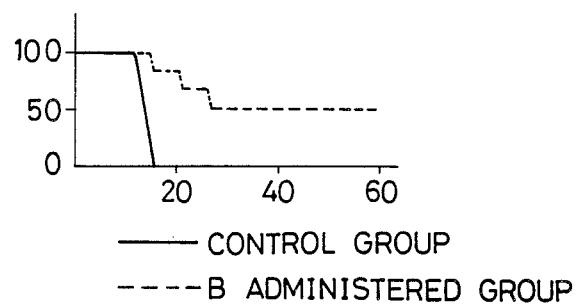

The effects of the medicines were judged from survival graphs (FIGS. 3 and 4) obtained from observation of the control group, administration group A, and administration group B for 60 days after the grafts of hepatoma cells. If a case in which the graph of each administration group was substantially the same as that of the control group, or in which rats died and the area under the curve was twice or less that of the control group, is denoted by (−); a case in which 50% or more of the rats recovered and the area was three times or less is denoted by (+); and intermediate cases are denoted by (±); both the administration groups A and B show (+).

However, the amount of the germanium compound contained in each of the compounds of the present invention is, for example, for the lysine salt, 46% of the same amount of the free germanium compound. Therefore, the salts of the present invention show activity degrees which are substantially the same as or higher than that of the same amount of free germanium compound, which means that the compounds of the present invention are extremely effective.

We claim:

1. A salt of an organogermanium compound comprising the following formula (1):

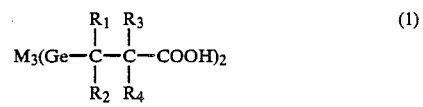

wherein M represents an oxygen or sulfur atom; and $R_1$, $R_2$, $R_3$ and $R_4$ which are the same or different, represent a hydrogen atom, a lower alkyl group or an aryl group; and a lysozyme or a basic amino acid.

2. The salt of an organogermanium compound according to claim 1, wherein said basic amino acid is L-lysine.

3. The salt of an organogermanium compound according to claim 1, wherein M is an oxygen atom.

4. The salt of an organogermanium compound according to claim 1, wherein $R_1$, $R_2$, $R_3$ and $R_4$ represent a hydrogen atom.

5. A pharmaceutical composition comprising an antitumor treating effective amount of a salt of an organogermanium compound having the following formula (1):

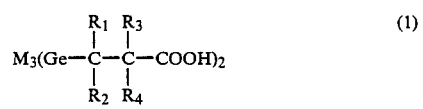

wherein M represents an oxygen or a sulfur atom; and $R_1$, $R_2$, $R_3$ and $R_4$ which are the same or different, represent a hydrogen atom, a lower alkyl group or an aryl group; and a lysozyme or a basic amino acid, and a pharmaceutically acceptable carrier therefor.

6. The pharmaceutical composition according to claim 5, wherein said basic amino acid is L-lysine.

7. The pharmaceutical composition according to claim 5, wherein M is an oxygen atom.

8. The pharmaceutical composition according to claim 5, wherein $R_1$, $R_2$, $R_3$ and $R_4$ represent a hydrogen atom.

9. A method of treating a tumor in a patient which comprises administering to a patient in need of such treatment an antitumor treating effective amount of a salt of an organogermanium compound having the following formula (1):

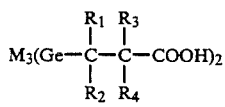

wherein M represents an oxygen or a sulfur atom; and $R_1$, $R_2$, $R_3$ and $R_4$ which are the same or different, represent a hydrogen atom, a lower alkyl group or an aryl group; and a lysozyme or a basic amino acid.

10. The method according to claim 9, wherein said basic amino acid is L-lysine.

11. The method according to claim 9, wherein M is an oxygen atom.

12. The method according to claim 9, wherein $R_1$, $R_2$, $R_3$ and $R_4$ represent a hydrogen atom.

13. A method for enhancing the bioavailability of an organogermanium compound of the formula (1):

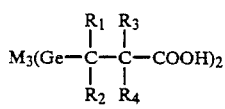

wherein M represents an oxygen or sulfur atom; and $R_1$, $R_2$, $R_3$ and $R_4$ which are the same or different, represent a hydrogen atom, a lower alkyl group or an aryl group; said method comprising adding to said organogermanium compound a basic amino acid or a lysozyme.

14. The method according to claim 13, wherein said basic amino acid is L-lysine.

15. The method according to claim 13, wherein M is an oxygen atom.

16. The method according to claim 13, wherein $R_1$, $R_2$, $R_3$ and $R_4$ represent a hydrogen atom.

17. A salt of an organogermanium compound comprising the following formula (1):

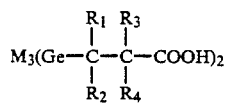

wherein M represents an oxygen or sulfur atom; and $R_1$, $R_2$, $R_3$ and $R_4$ which are the same or different, represent a hydrogen atom, a lower alkyl group or an aryl group; and a lysozyme.

18. The salt of an organogermanium compound according to claim 17, wherein M is an oxygen atom.

19. The salt of an organogermanium compound according to claim 17, wherein $R_1$, $R_2$, $R_3$ and $R_4$ represent a hydrogen atom.

20. A pharmaceutical composition comprising an antitumor treating effective amount of a salt of an organogermanium compound having the following formula (1):

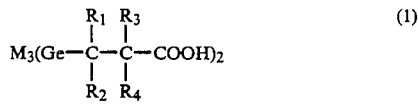

wherein M represents an oxygen or a sulfur atom; and $R_1$, $R_2$, $R_3$ and $R_4$ which are the same or different, represent a hydrogen atom, a lower alkyl group or an aryl group; and a lysozyme, and a pharmaceutically acceptable carrier therefor.

21. The pharmacuetical composition according to claim 20, wherein M is an oxygen atom.

22. The pharmaceutical composition according to claim 20, wherein $R_1$, $R_2$, $R_3$ and $R_4$ represent a hydrogen atom.

23. A method of treating a tumor in a patient which comprises administering to a patient in need of such treatment an antitumor treating effective amount of a salt of an organogermanium compound having the following formula (1):

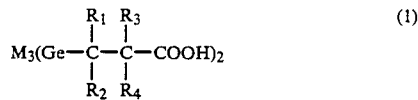

wherein M represents an oxygen or a sulfur atom; and $R_1$, $R_2$, $R_3$ and $R_4$ which are the same or different, represent a hydrogen atom, a lower alkyl group or an aryl group; and a lysozyme.

24. The method according to claim 23, wherein M is an oxygen atom.

25. The method according to claim 23, wherein $R_1$, $R_2$, $R_3$ and $R_4$ represent a hydrogen atom.

26. A method for enhancing the bioavailability of an organogermanium compound of the formula (1):

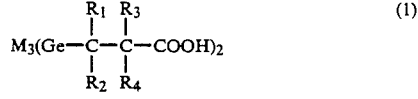

wherein M represents an oxygen or sulfur atom; and $R_1$, $R_2$, $R_3$ and $R_4$ which are the same or different, represent a hydrogen atom, a lower alkyl group or an aryl group; said method comprising adding to said organogermanium compound a lysozyme.

27. The method according to claim 26, wherein M is an oxygen atom.

28. The method according to claim 26, wherein $R_1$, $R_2$, $R_3$ and $R_4$ represent a hydrogen atom.

* * * * *